(12) United States Patent
Medina-Llamas et al.

(10) Patent No.: US 9,738,888 B2
(45) Date of Patent: Aug. 22, 2017

(54) MAGNETIC NANOCOMPOSITE RETRIEVAL OF NUCLEOTIDE SEQUENCE

(71) Applicant: UNIVERSIDADE FEDERAL DE PERNAMBUCO—UFPE, Recife (BR)

(72) Inventors: Juan Carlos Medina-Llamas, Recife-PE (BR); Alicia Elizabeth Chávez-Guajardo, Recife-PE (BR); Cesar Augusto Souza de Andrade, Varzea (BR); Kleber Goncalves Bezerra Alves, Recife-PE (BR); Celso Pinto de Melo, Casa Forte (BR)

(*) Notice: Subject to any disclaimer, the term of this patent is extended or adjusted under 35 U.S.C. 154(b) by 28 days.

(21) Appl. No.: 14/594,845

(22) Filed: Jan. 12, 2015

(65) Prior Publication Data

US 2015/0132758 A1 May 14, 2015

Related U.S. Application Data

(63) Continuation-in-part of application No. 12/934,216, filed as application No. PCT/BR2009/000117 on Mar. 23, 2009, now Pat. No. 8,932,485.

(30) Foreign Application Priority Data

Mar. 24, 2008 (BR) ...................... 0805991

(51) Int. Cl.
| | |
|---|---|
| C09K 11/06 | (2006.01) |
| A61B 5/055 | (2006.01) |
| A21D 6/00 | (2006.01) |
| A23C 3/00 | (2006.01) |
| C12Q 1/68 | (2006.01) |
| C12N 15/10 | (2006.01) |
| C12Q 1/70 | (2006.01) |
| B01J 20/26 | (2006.01) |
| B01J 20/06 | (2006.01) |
| B01J 20/28 | (2006.01) |

(52) U.S. Cl.
CPC .......... *C12N 15/1013* (2013.01); *B01J 20/06* (2013.01); *B01J 20/262* (2013.01); *B01J 20/28009* (2013.01); *B01J 20/28011* (2013.01); *C12Q 1/701* (2013.01); *C12Q 1/708* (2013.01)

(58) Field of Classification Search
CPC ...... C12Q 1/68; C12Q 1/701; C12N 15/1013; C07H 21/02; C09K 11/06; A61B 5/055; G01N 33/553

USPC .......... 252/301.33; 424/9.32; 435/6.1, 287.2; 436/501, 523, 525; 977/704, 773, 840, 977/902

See application file for complete search history.

(56) References Cited

U.S. PATENT DOCUMENTS

| | | | | |
|---|---|---|---|---|
| 5,582,988 A | * | 12/1996 | Backus | ............... C07K 14/005 435/5 |
| 6,126,839 A | * | 10/2000 | Kreader | .................. C12R 1/32 210/723 |
| 2005/0142567 A1 | | 6/2005 | Su et al. | |
| 2006/0263908 A1 | | 11/2006 | Hirai | |
| 2009/0123939 A1 | * | 5/2009 | Alocilja | .............. G01N 27/745 435/7.2 |
| 2011/0171749 A1 | * | 7/2011 | Alocilja | ................. B82Y 5/00 436/501 |

FOREIGN PATENT DOCUMENTS

WO    2006061835 A1    6/2006

OTHER PUBLICATIONS

Medina-Llamas et al, Use of magnetic polyaniline/maghemite nanocomposite for DNA retrieval from aqueous solutions, 2014, Journal of Colloid and Interface Science, 434, 167-174.*
Choy et al, Inorganic-biomolecular hybrid nanomaterial as a genetic molecular code system, 2004, Ad. Mater., 16, 1181-1184.*

* cited by examiner

*Primary Examiner* — Narayan Bhat

(57) ABSTRACT

Disclosed is a process for retrieval of nucleotide sequence. The process includes mixing iron chloride tetrahydrate with iron (III) chloride hexahydrate in solution; adding ammonium hydroxide to the mixture and stirring to form maghemite nanoparticles; stirring the maghemite nanoparticles in a solution with an inorganic acid, a surfactant and a monomer precursor of a conducting polymer; initiating polymerization of the monomer by adding the inorganic acid and an oxidizing agent to the stirred solution and further stirring to yield Polyaniline/maghemite nanocomposites; adding the nanocomposites to an first aqueous solution of the nucleotide sequence and stirring so as to electrostatically interact the nanocomposites with the nucleotide sequence; and weakening the electrostatic interaction between the nanocomposite and the nucleotide sequence to recover the nanocomposite independently of the nucleotide sequence.

11 Claims, 12 Drawing Sheets

FIGURES 10A-D

Table 1
Langmuir and Freundlich isotherms parameters for SS-DNA adsorption onto Pani/γ-Fe$_2$O$_3$ MNC.

| Langmuir constants | | | Freundlich constants | | |
|---|---|---|---|---|---|
| $q_m$ (mg/g) | $b$ (L/mg) | $R^2$ | $K_F$ (mg/g) | $1/n$ | $R^2$ |
| 75.2 | 6.3 | 0.98 | 43.2 | 0.2 | 0.74 |

FIGURE 17

Table 2
Comparison of Pani/γ-Fe₂O₃ MNC with other adsorbents of DNA.

| Adsorbent | $q_m$ (mg/g) | Adsorption time (min) | % Desorption | Desorption time (min) | |
|---|---|---|---|---|---|
| Hemoglobin modified Fe₃O₄@SiO₂ MNC | 27.9 | 15 | 68.3 | 15 | |
| Fe₃O₄/SiO₂ microspheres | ~1.2 | 10 | – | – | |
| M-MSN NPs | 121.6 | 1200 | 89.5 | 60 | |
| PEI-modified Fe₃O₄ magnetic nanobeads | 70 | 1 | – | – | |
| Fe₃O₄/SiO₂ | 43.1 | 8 | – | – | |
| [C₆MIM]-Br/Fe₃O₄ NPs | 19.8 | 2 | 96 | 30 | |
| Fe₃O₄@PANI microspheres | 2.1 | 40 | – | 40-60 | |
| Fe₃O₄@PPy microspheres | 2.6 | – | – | – | |
| PSG-NH₂@Fe₃O₄@SiO₂ | ~17 | – | 56.2 | – | |
| Pani/γ-Fe₂O₃ MNC | 75.2 | 10 | 94 | 2 | This work |

M-MSN: Magnetic mesoporous silica nanoparticles; PEI: Polyethylenimine; [C₆MIM]-Br: 1-hexyl-3-methylimidazolium bromide; PSG: poly(styrene-co-glycidyl methacrylate).

FIGURE 19

MAGNETIC NANOCOMPOSITE RETRIEVAL OF NUCLEOTIDE SEQUENCE

CROSS REFERENCE TO RELATED APPLICATIONS

The present application is a continuation-in-part (CIP) of and claims priority to currently pending U.S. patent application Ser. No. 12/934,216 filed on Mar. 23, 2011, titled "FLUORESCENT NANOPARTICLE COMPOSITES THEMSELVES, PROCESS FOR THE PREPARATION OF SUCH COMPOSITES, AND USE IN RAPID DIAGNOSIS SYSTEMS WITH AFFINITY TO BIOLOGICAL MOLECULES", which claims priority from International patent application Ser. No. PCT/BR2009/000117 filed on Mar. 23, 2009 (Expired), which claims priority from Brazilian patent application Ser. No. PI0805991-8 filed on Mar. 24, 2008. The entire contents of the aforesaid U.S. patent application, international application and the aforesaid Brazilian patent application being incorporated herein by reference.

FIELD OF THE INVENTION

The present invention refers to fluorescent nanoparticle composites. More specifically, it refers to the composites themselves, to the process of preparing such composites, systems for rapid diagnosis (as "kits") containing such composites, and to the use of such composites. Besides that, the composites of the present invention have an affinity for biological molecules, such as DNA and RNA, also providing for applications in the medical and veterinarian fields, and in the diagnosis of genetic diseases as well as those caused by several pathogens. The invention also pertains to the use of magnetism in nanoparticles for the retrieval of DNA, and for rapidly providing the DNA for the diagnosis.

BACKGROUND OF THE INVENTION

Molecular Diagnosis

The molecular diagnosis of diseases and genetic traits is an emerging field, particularly in the area of clinical analysis. Generally, it uses techniques from molecular biology for the study of DNA/RNA, of infectious agents, or of genetic changes in the organism itself, aiding in the diagnosis and prognosis of infectious and genetic diseases.

The more common molecular biology techniques currently used are: enzymatic amplification of the DNA (PCR), digestion of the genomic DNA strand or of PCR product with restriction enzymes, electrophoretic separation of the DNA or of the PCR product, hybridization of the DNA or PCR fragments with oligonucleotide probes, DHPLC and cytogenetic methods. These techniques allow the rapid genotyping of polymorphic markers, tracking of uncharacterized mutations. In particular, the cytogenetic methods, based on the microscopic observation of normal and abnormal chromosomes, allow the construction of cytogenetic maps of the genomes of many species. The FISH (fluorescent in situ hybridization) cytogenetic method is the most direct means of locating molecular and genetic markers in the cytogenetic map, allowing the integration between genetic and molecular markers. Probes are widely used for diagnosis, such as cosmid probes, which are unique sequences connected in small segments of certain chromosomes, being useful for the study of microdeletions. Other probes are used to detect translocations and highly repetitive sequences. However, one should point out that some of these techniques still have some limitations, such as false-positive signals, that can lead to an error in diagnosis.

A well-known molecular diagnosis system is the ELISA (Enzyme-Linked ImmunoSorbent Assay). This immune-enzymatic test allows the detection of specific antibodies in the serum of patients, being the first-line test in the diagnosis of HIV (human immunodeficiency virus) infection. The method for performing the test is based on the antibody-antigen interaction, with this test also being capable of detecting other substances, such as hormones.

The present invention refers to the fluorescent nanoparticle composites themselves, method for the preparation of these composites, system for rapid diagnosis (as "kits") containing such compounds, and functioning of said "kits". In particular, the composites of the present invention have specific characteristics regarding size and fluorescence, and have an affinity for biological molecules, such as DNA, RNA, and also proteins. The method for the preparation of these compounds is also described in the present invention. Plus, the present invention describes the method of preparation for an adequate probe (named here as "support") containing biological material of the organism one wishes to study. Upon this support the fluorescent nanoparticle composites and the patient's biological material are added, comprising a diagnostic system, designated here as the ELINOR (from "Enhanced Luminescence from Inorganic/Organic nanocomposites") test, for the diagnosis of diseases caused by several pathogens and/or genetic diseases, amongst other things. The present invention has application mainly in the medical and veterinarian fields.

The patent literature describes an ample variety of probes for the diagnosis of specific diseases. However, most of the documents deal with methods that use the PCR molecular biology technique, requiring the amplification of the biological molecule that one wishes to study in order to perform the diagnosis. One can exemplify the methods for the diagnosis of diseases by the documents presented below.

Document U.S. Pat. No. 6,258,570 deals with a method for the diagnosis of viral meningitis using PCR, as does document U.S. Pat. No. 7,041,255, which uses the same technique to detect infection by the dengue virus. Likewise, the PCR is used for the diagnosis of the human papilloma virus (HPV), as described by document U.S. Pat. No. 6,027,89, and of *Streptococcus pneumoniae*, as described by U.S. Pat. No. 6,869,767.

The present invention differs from all of those documents by not requiring a step of amplification (such as the one performed in the PCR technique) in order to perform the molecular diagnosis.

The patent literature also reveals several examples of fluorescent biosensors containing gold, out of which we highlight the most relevant.

Document US 2007/0059693 describes a biosensor containing a fluorescent surface, molecules of nucleic acid, and a fluophore. The fluorescent surface may be a metal, including gold. The molecules of nucleic acid must have one of the ends bound to the fluorescent surface and the other end to a fluophore. This molecule of nucleic acid may also have internal hybridization regions that, when hybridized, form a "staple". In these cases, the fluophore will be close to the fluorescent surface, allowing fluorescence to occur. The present invention differs from that document due to the support surface not being necessarily fluorescent or metallic, and not requiring that the molecules of nucleic acid form a "staple" in order to emit fluorescence.

Document US 2005/0196876 describes a method for the analysis of the content of a biological sample through the contact of the sample with a nanoporous biosensor. This biosensor contains probes that bind to the samples forming complexes that will be bound to a second probe. That probe will be illuminated so as to send a specific fluorescent signal. In an optional configuration, this biosensor may have a layer of gold. The present invention differs from the aforementioned document by dealing with fluorescent nanoparticles containing gold, there being no need to bind to more than one probe.

Document U.S. Pat. No. 6,773,884 describes a method for the detection of nucleic acids in which those molecules are put in contact with one or more nanoparticles of gold bound to oligonucleotides and to fluorescent molecules. When the hybridization occurs, the interaction of these molecules with the oligonucleotides suffers an alteration detectable as changes in the florescence. The present invention differs from the aforementioned document by dealing with nanoparticles in which the gold is covered by polymers, and by being deposited over the biological molecules studied, there being no need for the presence of oligonucleotides bound to the nanoparticle.

Document U.S. Pat. No. 7,083,928 describes the detection of negatively charged polymers using water-soluble cationic polythiophenes. The negatively charged polymers include biological molecules such as nucleic acid. This polymer may be bound to a conductive support, such as a gold surface. When the polymer is detected, there is a change in the electronic load, fluorescence, or color, The present invention differs from the aforementioned document by dealing with nanoparticles of gold covered by polymers that interact with the biological molecules, with the gold not being part of the adequate support that will immobilize the biological molecules.

Therefore, no document was found describing, nor suggesting, the fluorescent nanoparticle composites themselves, their form of preparation, the systems containing such composites for use in diagnostic "kits", or form of functioning for such systems.

DNA Retrieval

Extraction of DNA from cells and biological samples and its purification are of primary importance to the fields of molecular diagnostics, biotechnology and forensics. Further, extraction and purification of DNA are generally the first steps in the analysis and manipulation of DNA that allow scientists to detect genetic disorders, produce DNA fingerprints of individuals and prepare for therapeutical solutions.

In recent years, magnetic separation of DNA adsorbed on magnetic mesoporous silica nanoparticles has found increasing use as a technique for DNA retrieval. Magnetic separation is attained by adding magnetic nanoparticles (MNPs) to a solution containing the target molecule and allowing enough time for interaction between the target molecules and the MNPs to occur. Subsequently, the MNPs are spatially confined by the application of a non-uniform external magnetic field, resulting in a concentration of the target molecules. As reviewed in literature [Biotechnology Advances Volume 29, Issue 1, (2011) Pages 142-155 and "Biomaterials 26 (2005) Pages 3995-4021], the MNPs most frequently used to this end are magnetite ($Fe_3O_4$) and maghemite ($\gamma$-$Fe_2O_3$), due to their high saturation magnetization, low toxicity and biological compatibility. Laurent et al. have shown that the use of pure iron oxide particles has as a drawback—the tendency of these MNPs to form agglomerates. As such, it is usually necessary to modify the surface of the particles to prevent the self-aggregation [Chemical Reviews, 2008, 108 (6), pages 2064-2110]. However, such modification typically results in a loss of magnetic potency. Presently, materials offering sufficient magnetic properties while avoiding agglomeration have not been described in the prior art.

Therefore, there remains a need for low-cost, recyclable material for use in a fast, simple, and efficient method of DNA separation and concentration.

SUMMARY OF THE INVENTION

In one aspect, an embodiment of the present disclosure provides a process for retrieval of nucleotide sequence. The process comprises in solution, mixing iron chloride tetrahydrate with iron (III) chloride hexahydrate; adding ammonium hydroxide to the mixture and stirring to form maghemite nanoparticles; stirring the maghemite nanoparticles in a solution with an inorganic acid, a surfactant and a monomer precursor of a conducting polymer; initiating polymerization of the monomer by adding the inorganic acid and an oxidizing agent to the stirred solution and further stirring to yield Polyaniline/maghemite nanocomposites; adding the nanocomposites to an first aqueous solution of the nucleotide sequence and stirring so as to electrostatically interact the nanocomposites with the nucleotide sequence; and weakening the electrostatic interaction between the nanocomposite and the nucleotide sequence to recover the nanocomposite independently of the nucleotide sequence.

Optionally, mixing the iron chloride tetrahydrate with iron chloride hexahydrate comprises mixing in a molar ratio of 1:2.

Optionally, the process further comprises doping the nanocomposites with one or more acids.

Optionally, after recovering the nanocomposite independently of the nucleotide sequence, the nanocomposite is washed and acid doped then added to a second aqueous solution of nucleotide sequence and stirred so as to electrostatically interact the nanocomposite with the nucleotide sequence of the second solution.

Optionally, stirring the maghemite nanoparticles in a solution with hydrochloric acid, sodium dodecyl sulfate and a monomer further comprises stirring the maghemite nanoparticles in a solution with hydrochloric acid, sodium dodecyl sulfate and aniline.

Optionally, adding the inorganic acid and an oxidizing agent to the stirred solution further comprises adding ammonium persulfate to the stirred solution.

Optionally, stirring the maghemite nanoparticles in a solution with an inorganic acid, a surfactant and a monomer precursor of a conducting polymer further comprises stirring in a solution with sodium dodecyl sulfate.

Optionally, stirring the maghemite nanoparticles in a solution with an inorganic acid comprises stirring with hydrochloric acid.

Optionally, weakening the electrostatic interaction between the nanocomposite and the nucleotide sequence to recover the nanocomposite independently of the nucleotide sequence comprises weakening with a solution of an alkali salt.

Optionally, weakening with a solution of an alkali salt comprises weakening with a solution of sodium hydroxide.

Optionally, electrostatically interacting the nanocomposites with the nucleotide sequence further comprises electrostatically interacting with DNA or RNA.

In one aspect, an embodiment of the present disclosure provides a biological diagnosis kit for rapid patient diagnosis. The kit comprises at least one composite; at least one short nucleotide sequence; an appropriate substrate for the immobilization of the short nucleotide sequence; and a genetic sample of the patient.

Optionally, the composite of the biological diagnosis kit further comprises at least one magnetic nanoparticle and at least one conducting polymer.

Optionally, the magnetic nanoparticle of the biological diagnosis kit comprises maghemite.

Optionally, the at least one conducting polymer of the biological diagnosis kit comprises polyaniline.

Optionally, the short nucleotide sequence of the biological diagnosis kit comprises RNA or single-stranded DNA.

Optionally, the substrate of the biological diagnosis kit comprises a glass slide, paper and/or a polymer strip.

Optionally, the at least one composite comprises a fluorescent composite.

In one aspect, an embodiment of the present disclosure provides a DNA-bonding nanocomposite. The DNA-bonding nanocomposite comprises at least one oxidizing agent; at least one stabilizer agent; and at least one conducting polymer.

Optionally, the oxidizing agent of the DNA-bonding nanocomposite comprises iron chloride tetrahydrate with iron (III) chloride hexahydrate.

Optionally, the conducting polymer of the DNA-bonding nanocomposite is polyaniline (Pani).

These and objects of the present invention will be better understood and properly appreciated after analysis of the detailed description of the invention and the corresponding accompanying claims.

BRIEF DESCRIPTION OF THE FIGURES

FIG. 17 is a table representing Langmuir and Freundlich isotherms parameters for SS_DNA adsorption onto Pani/$\gamma$-$Fe_2O_3$ MNC.

FIG. 19 is a table representing a comparison of characteristics of various DNA adsorbents including Pani/$\gamma$-$Fe_2O_3$.

DETAILED DESCRIPTION OF THE INVENTION

Figure 1:
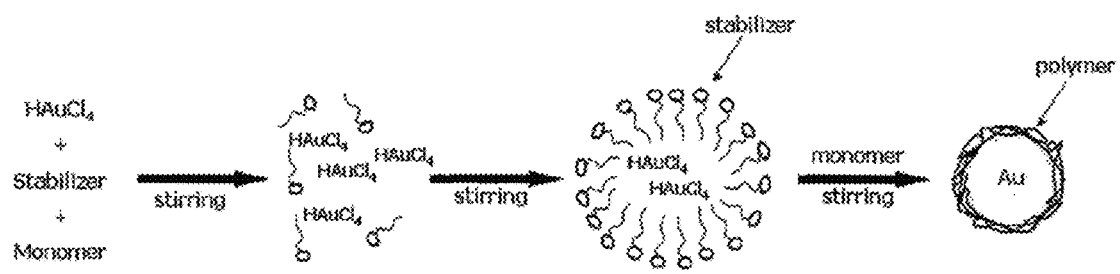
FIG. 1 is a schematic representation of the preparation route to obtain the fluorescent composites ((Au nanoparticles)/(conducting polymer)).

The composites of the invention are useful for different applications, including: the preparation of photovoltaic devices, such as solar cells, and electroluminescent devices, as organic LEDs, leading in both cases to a substantial increase in their quantum efficiency; the increase in the lighting efficiency of fluorescent lamps; the preparation of reagents and consumable items for diagnosis procedures, amongst other applications. The composites of the present invention provide, among other advantages, the absorption of incident light in the ultraviolet or visible regions and the emission of light in the ultraviolet and visible region, inclusive in the "deep blue" and/or green colors, providing a special advantage in their use in photovoltaic devices, such as solar cells, or in electroluminescent devices, as organic LEDs, or for the increase in the quantum yield of lighting systems, such as fluorescent lamps. In regard to the latter application, the composites of the present invention provide an environmentally friendlier and more energy efficient alternative to the phosphors presently used in the internal layer of coverage of fluorescent lamps to assure the ultraviolet quantum cut-off and that are a source of pollution when not properly discarded. The composites of the invention can be prepared so as to provide emission in different colors and with wide-range adjusting intensities, according to the tuning of their composition and preparation manner.

The composites of the present invention have affinity for biological molecules, such as DNA, RNA, or proteins, providing also applications in the areas of human and animal health and in the diagnosis tests for diseases caused by different pathogenic agents. In this regard, the following examples do not have the purpose of limiting the range of the invention, but rather only illustrate one of the innumerable manners of realizing the invention.

It is understood by "biological material" the group of compounds that comprises, but it is not limited to, DNAs, RNAs, proteins, lipids, peptides, non-codifying RNAs, and/or any other biological material that could be represented by a single chain or single strand.

It is understood by "genetic material of the patient" the group of biological material that comprises, but it is not limited to, the biological material of any organism that could be present in a small amount of blood or obtained from a simple collection of epithelial or mucosa cells, and/or from secretions and/or excretions of the patient. It is understood by "oxidizing agent" is a salt in which the cation is selected from the group comprising metals chosen from groups 1B to 8B of the periodic table. This group of compounds comprises, but it is not limited to, to gold compounds, such as $HAuCl_4$. Preferentially, the gold atom is in the 3+ oxidation state. However, other salts of metals of the 1B to 8B families can be used, provided that their oxi-reduction potential allows the oxidation of the monomer, leading to the formation of the polymer. The present inventors have prepared other compounds not only based on Au, but also on Ag and Cu, and using other monomers besides pyrrole, such as derivatives of aniline and thiophene. In a similar way, the experts in the field will understand that metals such as nickel, platinum and palladium can also be used. The present inventors have also prepared other composites in which the conducting polymer was used in the presence of metallic oxides, in such manner as to obtain composites that exhibit at the same time properties of fluorescence and magnetism. It is understood by metallic oxides, compounds, the general class of compounds containing oxygen and metals, such as, but not limited to, iron and titanium. It is understood by "monomer" any compound that can be polymerized by the oxidizing agent. Namely, it is chosen from the group that comprises, but it is not limited to, the smallest repetitive unit of a polymer, as those derived from aniline ($C_6H_5NH_2$), thiophene ($C_4H_4S$), pyrrole ($C_4H_5N$), or precursor molecules of the respective polymers, PANI, PEDOT ((poly(3, 4-ethylenedioxythiphene)poly(styrenesulfonate)), PTAA (polythiophene acetic acid) and polypyrrole, and/or a mixture of these.

It is understood by "stabilizing agent", the group of compounds that comprises, but it is not limited to, silanes, such as (3-mercaptopropyl)trimethoxy silane (MPS), (3-mercaptopropyl)methyldimethoxysilane, (3-mercaptopropyl) triethoxysilane e (3-mercaptoethyl)trimethoxysilane and/or a mixture of them.

It is understood by "alcohol" the group that comprises, but it is not limited to methanol, ethanol, propanol, butanol, glycerol, ethylene glucol and/or a mixture of them.

EXAMPLE 1

Synthesis and Characterization of the Nanoparticles

EXAMPLE 1.1

Preparation of the Nanoparticles

The preparation of nanoparticles was performed (see scheme in FIG. 1) in a round bottom glass flask containing ethanol (20 mL) and the compounds: aniline (Ani-$C_6H_5NH_2$) (0.030 mol/L), 3-mercaptopropyl-trimethoxy-silane (MPS-$C_6H_{16}O_6SSi$) ($6.46 \times 10^{-2}$ mol/L) and $HAuCl_4.xH_2O$ (0.81 mmol/L), which were subsequently added and subject to energetic agitation (1,100 rpm). Aniline (Ani-$C_6H_5NH_2$) was acquired from VETEC (Brazil) and only used after distillation in a Kugelrohr apparatus. The other compounds were bought from Aldrich Co. (USA), and had at least 99% degree of purity. All subsequent experiments were performed in the 48 hours' time interval after the mixtures.

EXAMPLE 1.2

Characterization of the Nanoparticles

Photoluminescence properties were measured by use of a quartz cuvette (1 cm and 5 mL) in a PC1 (ISS, USA) spectrofluorimeter at (20±1°) C. The samples were monitored at different pH values by use of two luminescence matrices: (1) in the 200 to 360 nm excitation range and emission in the 370 to 600 nm interval; and (2) in the 270 to 330 nm excitation range and emission in the 280 to 600 nm interval. Morphological analyses were performed by scanning electron microscopy (SEM), by use of a JSM-5900 (JEOL, Japan) electron microscope. The samples were placed atop a glass substrate and fixed by a carbon tape. After this, the samples were covered by a thin gold layer by use of a sputtering (BalTec SCD 050). The size of the particles was determined by a light-scattering method by use of a Zetasizer Nano-ZS90 instrument (Malvern).

EXAMPLE 2

Characteristics of the Nanoparticles

Figure 2:
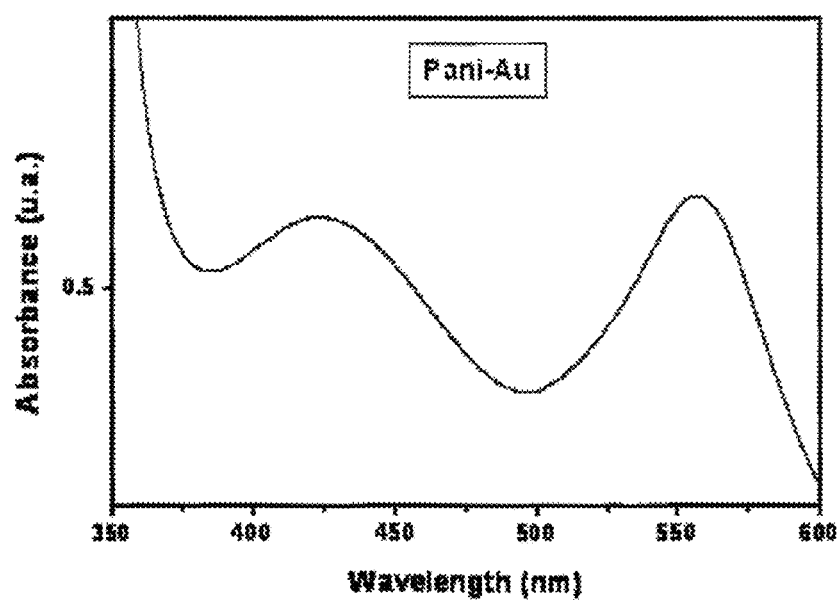
FIG. 2 is the UV-Visible absorption spectrum of the gold/polyaniline (Au/PANI) composites, where the plasmon band (associated to the reduced gold forming metallic nanoparticles) and the polaron band (associated to the monomer oxidation process leading to the formation of the polymer).

Gold nanoparticles with diameters of the order of ~5 nm exhibit in their absorption spectrum a surface plasmon (SP) band centred in 525 nm. The UV-Vis spectrum of the composites is shown in FIG. 2, where once can observe the strong presence of a SP band at 560 nm. It is known that the wavelength and the intensity of the SP band vary according to the size, shape and the "interparticle" dielectric medium, and that it is also sensitive to the relative molar fraction (stabilizing agent)/Au [*J. Am. Chem. Soc.* 2003, 125, 9906]. It is also known that (PANI) exhibit two characteristic absorption bands (324 nm and 625 nm) in the UV-Vis region.

In the method used in the present invention, the gold containing compound ($HAuCl_4.xH_2O$) acts as an oxidizing agent, i.e., the trigger of the aniline polymerization, while a mercapthosilane is included as a co-stabilizer of the formed metallic nanoparticles. In the fluorescence matrix of the PANi-Au sample, one can verify that the composite exhibit luminescent properties in the visible region, since the composite presents a peak of photoluminescence centred close to 400 nm when excited in the ultraviolet (350 nm) region. The use of gold nanoparticles and conducting polymers in light emitting diodes, while trying to increase the electroluminescence stability and quantum yield, was discussed in a recent paper [Chem. Mater.: 2004, 16, 688-692], where it is proposed that the reason for the observed effects are the increased roughness of the metallic cathode surface and the improvement of the balance of the injected charges promoted by the metallic nanoparticles. On the other hand, examples of water soluble and highly luminescent nanoparticles were recently published [Physical Review Letters vol. 93(7) 2004, pp. 77402-1 77402-4], where the intense luminescence was attributed to the formation of metallic aggregates that would lead to the injection and transport of charge through the discrete levels of energy. Differently from the above related examples, in the present case the method used has allowed the inventors to prepare gold nanoparticles with sizes of the order of 5 nm (or less), enveloped by a "shell" of conducting polymers, whose dielectric properties can be changed by varying either their oxidation state and/or the pH of the medium where they are dispersed. In this manner, at least in principle one can tune the emission wavelength of the composite by properly adjusting the dielectric properties of the medium. Measurements of the quantum yield of the first samples of the composites have indicated values in the 1.5 to 7.5% interval; however, modifications in the method of preparation already implemented have allowed the inventors to increase the quantum yield, as well as emission of the same system in different wavelengths.

Figure 3:
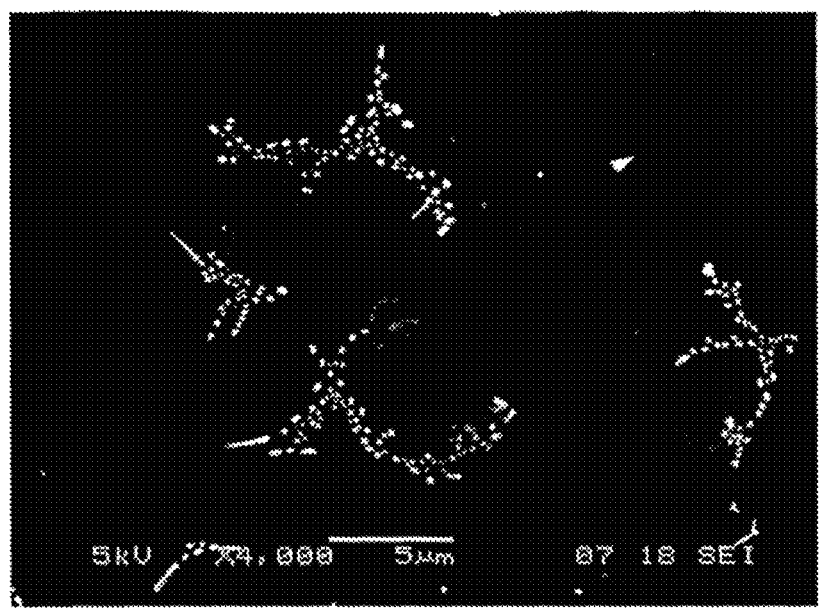
FIG. 3 is a scanning electron microscope image of the fluorescent composites (Au nanoparticles)/(conducting polymer). (Magnifying factor of 4,000×).
Figure 4:
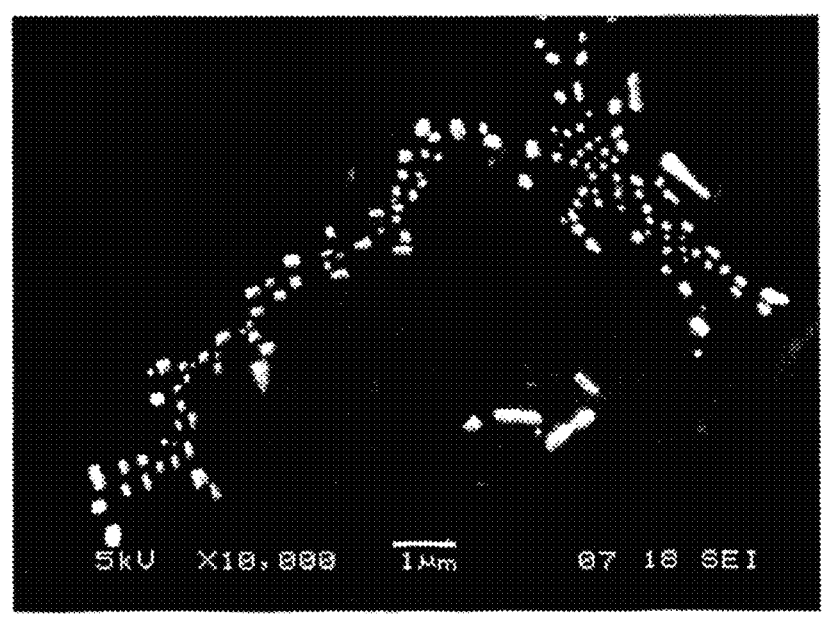
FIG. 4 is a scanning electron microscope image of the fluorescent composites (Au nanoparticles)/(conducting polymer). (Magnifying factor of 10,000×).

Scanning electron microscopy (SEM) shows that the nanoparticles tend to align themselves in more complex structures (FIGS. 3 and 4).

Figure 5:
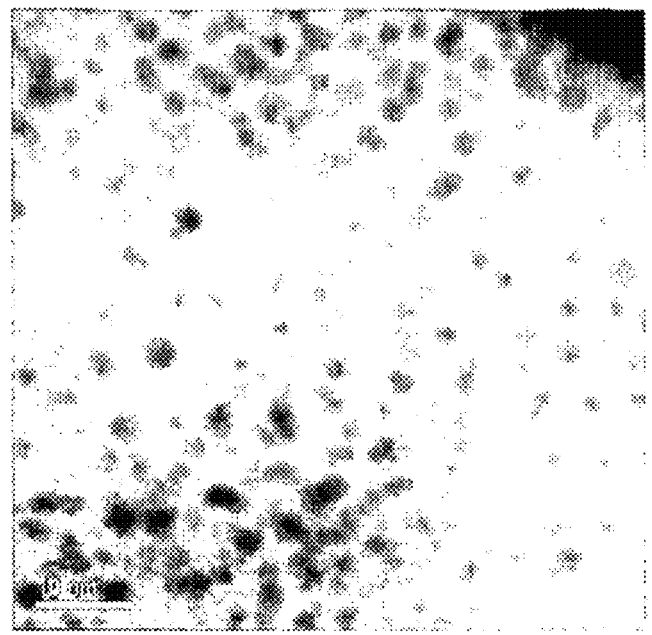
FIG. 5 is a transmission electron microscope image of the fluorescent composites (Au nanoparticles)/(conducting polymer).
Figure 6:
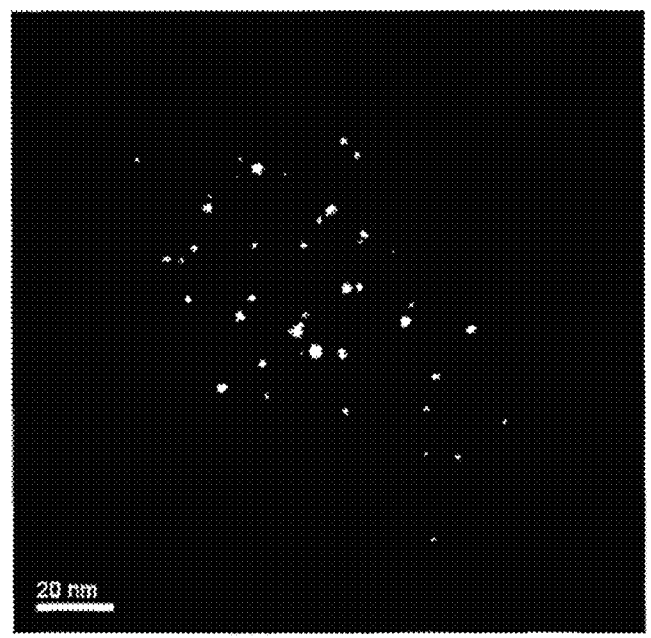
FIG. 6 is a transmission electron microscope image in dark field of the fluorescent composites (Au nanoparticles)/(conducting polymer). The lighter regions indicate the presence of metallic nanoaggregates enveloped by the polymeric chains.

Transmission electron microscopy (TEM) images in bright field were obtained for the composites object of the present invention (FIG. 5), where one can identify the presence of agglomerates with an average diameter of 50 nm. In addition, in the dark field mode, one can clearly see a regular and homogeneous distribution of gold nanoparticles (FIG. 6). It is important to stress that in light scattering experiments the average size of the agglomerates of the composites was estimated to be in the 150 to 300 nm range.

Figure 7:
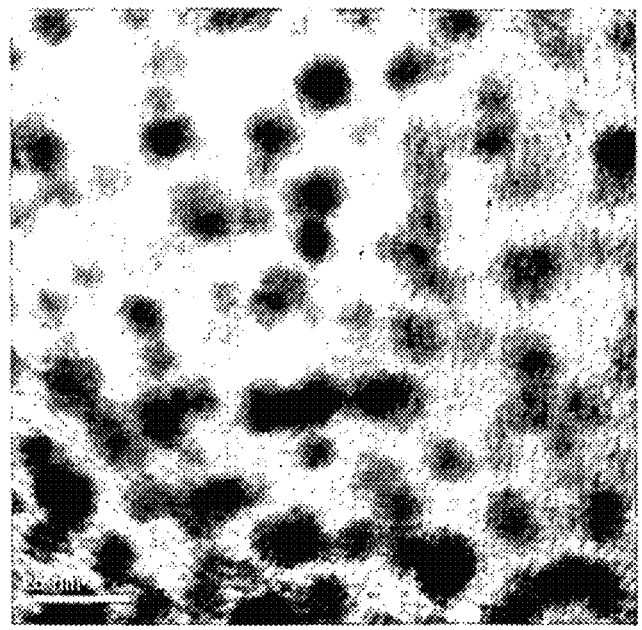
FIG. 7 is a transmission electron microscope image of the fluorescent composites (Au nanoparticles)/(conducting polymer) where the metallic nanoaggregates can be seen.
Figure 8:
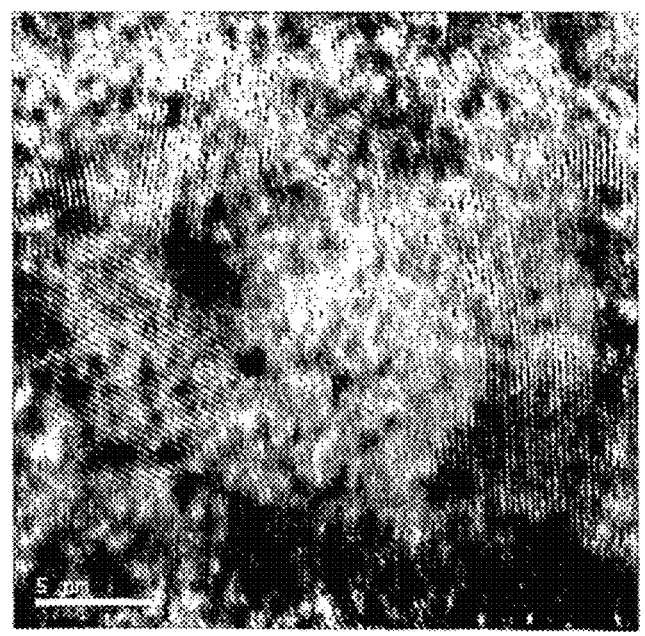
FIG. 8 is a high-resolution transmission electron microscope image of the fluorescent composites (Au nanoparticles)/(conducting polymer).
Figure 9:
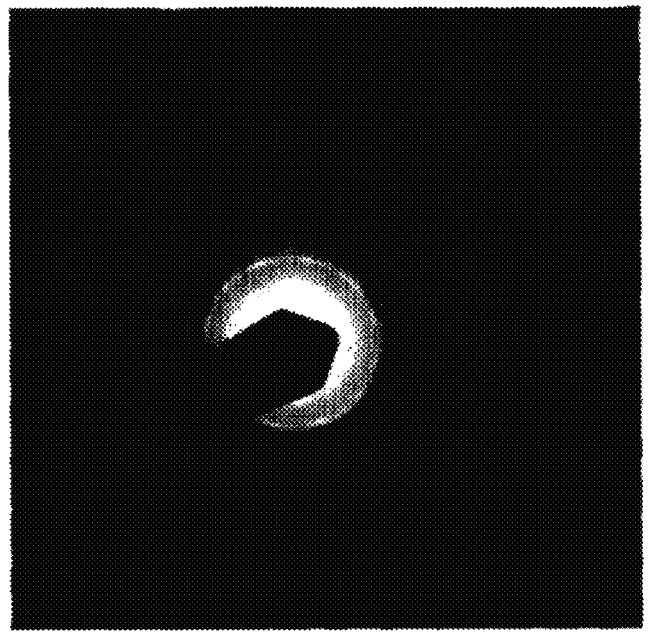
FIG. 9 is a X-ray diffraction image of the fluorescent composites (Au nanoparticles)/(conducting polymer).

FIG. 7 reveals that there is a monodisperse distribution of nanoparticles of sizes varying from 2 to 5 nm, even though in some cases formation of geminal particles—a well-known characteristic of gold nanoparticles—could be identified. A High Resolution Transmission Electron Microscopy (HR-TEM) image of the hybrid gold/(conducting polymer) nanocomposite reveals the presence of crystalline structures (FIG. 8), an observation that is confirmed by examining the corresponding X-ray diffraction (XRD) pattern (FIG. 9).

EXAMPLE 3

Diagnosis Kits Containing the Fluorescent Nanostructured Composites

Due to the fact that it is possible to adapt the methodology proposed in the present invention to large scale production with low capital investment and at a very price per unit, the associated technology has its low cost and speed of implementation as principal comparative advantages over the methods usually adopted in the diagnosis of infectious diseases caused by bacteria or virus, factors that accompanied by a greater generality and flexibility of application. One can identify some important characteristics of the use of the fluorescent nanocomposites in diagnosis kits:

(1) the specifity towards the presence of a given pathogenic agent is determined by the nature of the fragment of the biological material (such as a DNA single strand) immobilized in the probe, so that the technique do not is limited on that regard, and can be used for the identification of any organism for which a specific short sequence of biological material, such as DNA, can be obtained;

(2) the technology is of general use for the diagnosis of any disease: whose origin can be: a) attributed to a known pathogenic agent, or b) associated to the presence of a specific sequence of biological material (such as DNA or RNA), even if human (and so it opens the possibility of using the technology for the investigation not only of diseases already installed but also for the analysis of genetic tendency of patients with regard to the future development of hereditary pathologies;

(3) the amount of biological material to be used in the diagnosis assays is extremely small (e.g., a volume of 1 µL of a 100 pmol solution of biological material, such as DNA);

(4) the preparation of the probes containing the sequence of the biological materials (such as DNA) is a step that can be adapted to large scale production, once again at a very low cost;

(5) the manipulation of the genetic material obtained from the patient to use in the proposed diagnosis procedure do not require steps related to separation and amplification of the DNA of interest, via polymerase chain reaction (PCR) and similar techniques;

(6) the result of the diagnosis assay has a conclusive character (i.e., positive/negative) and it can be obtained in a matter of minutes, with no need of using any kind of culture medium;

(7) the result of the diagnosis assay is based in the observation of the intensity of the fluorescence signal, indicating the presence or absence of the nucleotide sequence of interest;

(8) in the case of existence of genetic variation of the pathogenic agent in different subtypes (as in the case of the dengue virus, for example), the assay probe can be prepared in such manner as to contain biological material of each subtype to be investigated, and hence a single test can provide a conclusive answer with regard to the presence of any variety of the pathogen in the genetic sample provided by the patient;

(9) in the case in which the symptoms exhibited by the patient can be attributed to a limited number of possible pathogenic agents (as, for example, in the case of hospital acquired infections, or in the case of victims of accidents with deep perforations and wounds), the probe can be prepared in such manner as to contain biological materials (nucleotide sequence) of each one of the agents, so that in a single and rapid exam the diagnosis can be conclusive for the presence of any of them;

Since this technology can be applied to the diagnosis of the presence of any pathogenic agent, one can choose the nature of the microorganism to be investigated in appropriated tests, defined from the problems of possible interest for the public health of a given country or region. The rapid diagnosis kit here proposed can be used, but is not limited, to the diagnosis of: dengue virus: ii) tuberculosis; iii) hepatitis C; iv) human papillomavirus (HPV), v) leishmaniasis, vi) rapid identification (from within a pre-selected range of options) of the cause of hospital acquired infections; vii) rapid identification of meningococcus infections; viii) bioterrorism hazards, besides ix) genetic screening of hereditary diseases (such as Tay-Sachs, phenylketonuria, breast cancer, among others). A few examples are discussed below.

EXAMPLE 3.1

Diagnosis of the Presence of the Human Papillomavirus, HPV

The diagnosis procedure uses a short sequence of a single nucleotide strand consisting of 20 bases of the variety 16 of HPV. The quality of the response can be attested when a negative answer was obtained whenever the probe was exposed to a double strand of the variety 18 of HPV with circa of 500 base pairs and a positive answer only when the probe was exposed to double strand with 500 bases pairs of the variety 16 of HPV.

EXAMPLE 3.2

Diagnosis of the Presence of the Dengue Virus

The diagnosis procedure uses a short single strand consisting of 22 bases of the subtype 2 of the dengue virus. The quality of the response is associated to a negative answer when the probe was exposed to a double strand non-complementary to the original sequence used and to a positive diagnosis when the probe was exposed to a double strand containing 22 base pairs of the subtype 2 of the virus dengue.

EXAMPLE 3.3

Diagnosis of the Presence of the Human Papillomavirus (HPV) and the Sensitiveness of the Response to the Presence of Alleles The diagnosis procedure uses short single strand sequences of 19 (MBL54mt) and 22 (MBL57mt) bases corresponding to human lectin responses to different HPV varieties, some of them containing mutations in specific positions that could block the hybridization of the DNA chains of the pathogenic agent present in the material of the patient. The type of response (positive or negative answer) obtained, respectively, for homozygous and heterozygous patients define the sensitiveness of the technology as excellent.

In all of the examples above referred, a short sequence of a single strand of nucleotide chain (DNA or RNA) was anchored atop a previously silanized glass substrate, and afterwards a small drop of the mixture (composite (metal nanoparticle)/(conducting polymer)+(total DNA of the patient)) was added. The system was subsequently washed with running distilled water and, after waiting for about three minutes for drying, the substrate was placed in a fluorescence microscope for analysis. In case of existence of genetic material of the pathogenic agent in the biological material obtained from the patient (the "total DNA"), a long nucleotide strand of the pathogenic agent will hybridize to the immobilized short sequence, and retain a larger amount of fluorescent composite: a "positive" answer will then arise. If the hybridization did not occur, only a smaller amount of the composite Will remain attached to the short immobilized sequence of nucleotide, and as a consequence the fluorescence signal will be minimum (basal): the "negative" answer. It has to be noted that in a series of tests with the HPV, one of the 20 bases was deliberately altered, changing an original "positive" answer to "negative"; hence, the sensitiveness of the here proposed procedure is able to discriminate the change of a single base in 20.

Yet other applications of the composites object of the present invention can be immediately apprehended by the experts in the field, once they have been exposed to the present information. Among others, one can call attention to the rapid in situ diagnosis in situations such as: diagnosis of diseases in the battlefield; rapid identification of anthrax and other forms of bioterrorism contamination; biological contamination of food and beverage products in general, as in the case of control of quality of grains and cereals; biological assays in the field for in situ identification and comparative analysis of specimens with regard to pre-selected biological characteristics (screening in the field or biobarcoding), eliminating the need of collecting and transporting redundant material; and methods of forensic identification. In regard to the last subject, the composites of the present invention can act as "nanoluminol"; a fairly recent publication of the University of San Diego, available in http://www.topnews.in/health/handheld-dna-detector-may-soon-be-reality-21411, shows that DNA portable detectors may offer substantial advantages over the present technology. Even though the technology adopted in such reference is much more complex and expensive (ion-selective field-effect transistor—ISFET) than that discussed in the present invention, it is an important example of the actual need of new developments this area of expertise.

EXAMPLE 4

Synthesis of Nanoparticles (for DNA Retrieval)

Magnetic nanoparticles and nanocomposites according to the present disclosure offer use in nucleotide retrieval such as DNA retrieval, RNA retrieval or both as further explained in greater detail in conjunction with following Examples. In an embodiment, the present disclosure provides a DNA-bonding nanocomposite for DNA retrieval. Primarily, the DNA-bonding nanocomposite is composed of an oxidizing agent, a stabilizing agent and a conducting polymer. In an example, the oxidizing agent is iron chloride tetrahydrate ($FeCl_2.4H_2O$) with iron (III) chloride hexahydrate ($FeCl_3.6H_2O$). In an example, the conducting polymer includes PANI.

EXAMPLE 4.1

Synthesis of $\gamma$-$Fe_2O_3$ (Nanoparticles for DNA Retrieval)

In one example preparation of a DNA-bonding nanocomposite, capable of DNA retrieval, maghemite (gamma-iron oxide; $\gamma$-$Fe_2O_3$) nanoparticles (NPs) may be prepared as follows: 50 mL of $FeCl_2.4H_2O$ and $FeCl_3.6H_2O$ solution is made in a molar ratio of 1:2, and then mixed in a 250 mL round-bottom flask under vigorous stirring for 10 min. After that, 125 mL of an aqueous solution of $NH_4OH$ (50 vol %) may be added quickly and the resulting solution stirred for 2 h. Next, the freshly formed NPs may be decanted with the help of a handheld magnet. Subsequently, the resulting material may be washed with deionized water, and the magnet used to once more decant the $\gamma$-$Fe_2O_3$. Repeating this process a number of times, for example four, minimizes contamination by any non-magnetic impurity. Finally, the NPs are dried in a vacuum oven at 60 C for 48 h to obtain a brown powder.

EXAMPLE 4.2

Synthesis of Pani/$\gamma$-$Fe_2O_3$ Magnetic Nanocomposite

In one example preparation of a DNA-bonding, magnetic nanocomposite, Pani/$\gamma$-$Fe_2O_3$ (MNC) is obtained through polymerization carried out in a 250 mL round-bottom flask. 100 mL of a 0.1M HCl solution, 60.7 mM of sodium dodecyl sulfate, 0.06 g of $\gamma$-$Fe_2O_3$ NPs and 1.5 mM of aniline added to a flask are stirred for 15 min. After stirring, 20 mL of a 0.1 M of HCl and 1.5 mM of ammonium persulfate (APS) may be slowly added to initiate polymerization. Allowing polymerization to proceed for 24 h at room temperature under stirring results in a green solution. After washing several times with methanol and deionized water the obtained product may be magnetically decanted, washed with HCl (0.1 M) to assure the acidic doping of the polymer, and then dried in a vacuum oven at 40 C for 24 h. As such, a dark green powder form of Pani/γ-$Fe_2O_3$ magnetic nanocomposite may be finally obtained.

EXAMPLE 4.3

Characterization of γ-$Fe_2O_3$ NPs and Pani/γ-$Fe_2O_3$ MNCs

Figure 10:
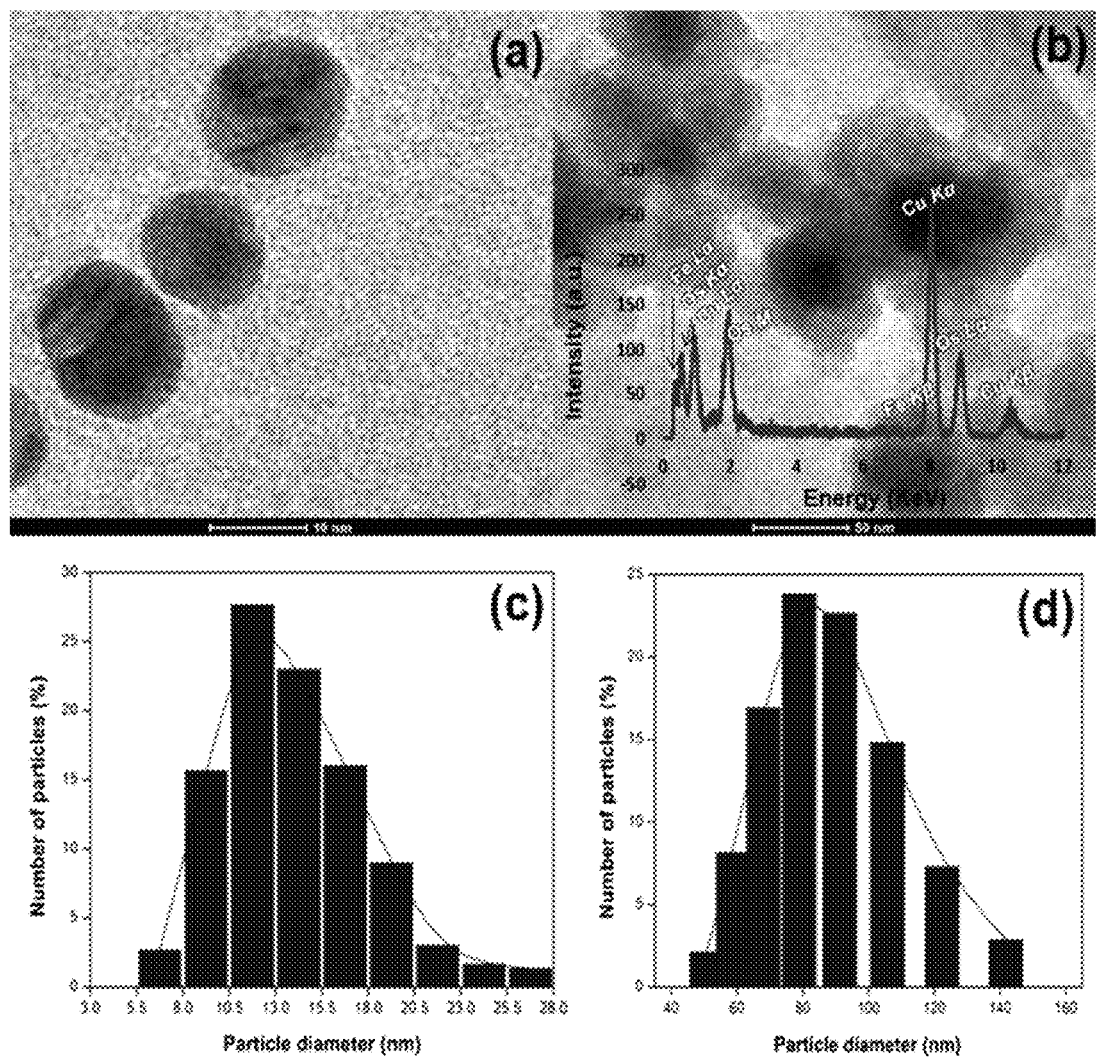
FIG. 10A is a Transmission Electron Microscopy (TEM) micrographs of $\gamma$-$Fe_2O_3$ nanoparticles (NPs) (a) and PANI/$\gamma$-$Fe_2O_3$ maghemite nanocomposite (MNC).
FIG. 10B is inset: Energy Dispersive Spectroscopy (EDS) spectrum of the MNC, specifically, histogram of the particle size of the $\gamma$-$Fe_2O_3$ NPs obtained after estimating the diameter of 300 particles depicted in several TEM micrographs.
FIG. 10C is a histogram of the particle size of the Pani/$\gamma$-$Fe_2O_3$ MNC obtained through Dynamical Light Scattering (DLS).
FIG. 10D is another histogram of the particle size of the Pani/$\gamma$-$Fe_2O_3$ MNC obtained through DLS.

When Transmission Electron Microscopy (TEM) is used to assess the size and the morphology of γ-$Fe_2O_3$ NPs and Pani/γ-$Fe_2O_3$ MNCs produced according to the above methods, nearly spherical morphologies are exhibited with individual sizes in the nanoscale range as presented in the γ-$Fe_2O_3$ NP TEM micrograph of FIG. 10a and the Pani/γ-$Fe_2O_3$ MNC TEM micrograph of FIG. 10b. Particle size distribution obtained using the ES Vision software version 5.0 [FEI & company. ES Vision software. Version 5.0 (2006)] estimates the diameter of each one of 300 γ-$Fe_2O_3$ NPs, as depicted in several TEM micrographs. Particle diameters are represented in the histogram plot of FIG. 10c, where it may be observed that the γ-$Fe_2O_3$ NPs have a size distribution of 5.5-28.0 nm, with an average diameter value of (14.0±7.5) nm. In the case of the TEM micrograph of the Pani/γ-$Fe_2O_3$ MNC (as shown in FIG. 10B), initially it is not possible to directly observe the Pani in the MNC since polymers usually have low electron densities. Hence, using $OsO_4$ as a contrast agent [Scanning Electron Microscopy and X-Ray Microanalysis, Klumer Academic/Plenum, 2003] followed by staining the polymer, makes it possible to observe the presence of a pattern of repeating dark and light regions. The dark regions appear to have one or more γ-$Fe_2O_3$ NPs, with the lighter regions corresponding to the Pani. To be sure of the presence of γ-$Fe_2O_3$ NPs in the MNC, an Energy Dispersive Spectroscopy EDS analysis confirms the presence of Fe and O in a sample. The micrographs reveal not only that the Pani chains envelope the γ-$Fe_2O_3$ NPs but also that the size of the Pani/γ-$Fe_2O_3$ MNC is in the nanoscale. The composite diameters are represented in the histogram plot of FIG. 10d, where it may be observed that the Pani/γ-$Fe_2O_3$ MNCs have diameters ranging from 50 nm to 142 nm with an average diameter value of (87±32) nm, as determined from DLS measurements.

Figure 11:
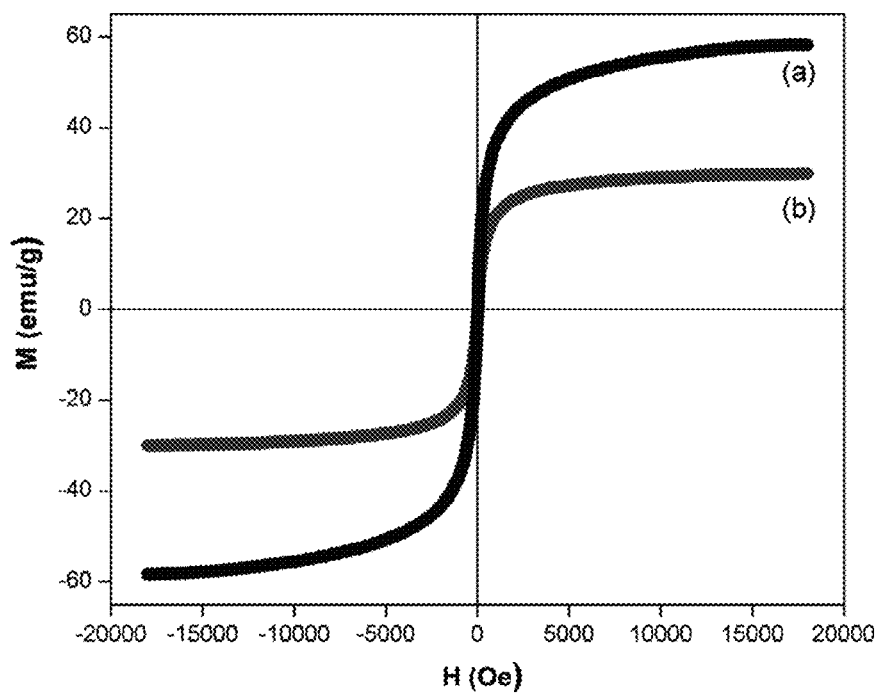
FIG. 11 is the room temperature magnetization curves of $\gamma$-$Fe_2O_3$ NPs (a) and Pani/$\gamma$-$Fe_2O_3$ MNC (b).

For a more quantitative assessment of the magnetic behaviour of the γ-$Fe_2O_3$ NPs and of the Pani/γ-$Fe_2O_3$ MNC, the corresponding magnetization curves, as shown in FIG. 11, are established. It may be observed from the magnetization curves that γ-$Fe_2O_3$ NPs exhibit a superparamagnetic behaviour at room temperature with a saturation magnetization (Ms) of 60 emu/g (curve a). Furthermore, Pani/γ-$Fe_2O_3$ MNC (30 emu/g) exhibits an Ms lower than that for the γ-$Fe_2O_3$ NPs (curve b). This observed decrease in the value of Ms is consistent with the fact that, while magnetization measurements take into account the total mass of the sample, the Pani chains do not contribute to the final Ms value.

Figure 12:
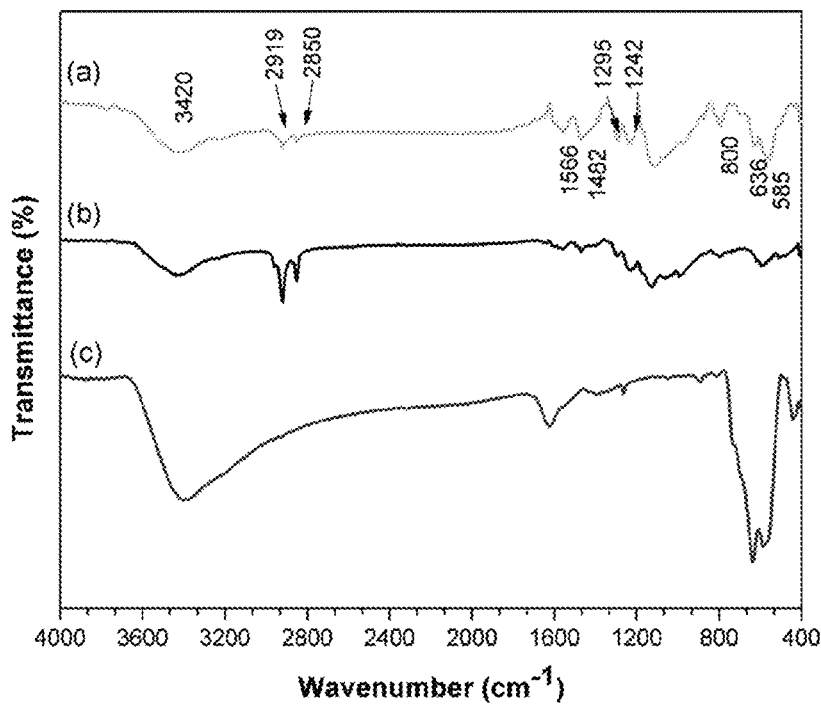
FIG. 12 is Fourier Transform Infrared Spectroscopy (FTIR) spectra of Pani/$\gamma$-$Fe_2O_3$ MNC (a), Pani (b) and $\gamma$-$Fe_2O_3$ NPs (c).

Additionally, a Fourier Transform Infrared Spectroscopy (FTIR) analysis for use as an auxiliary technique for determining the composition of the γ-$Fe_2O_3$ NPs and Pani/γ-$Fe_2O_3$ MNC samples is presented in FIG. 12. It may be observed that the Pani/γ-$Fe_2O_3$ MNC spectrum (curve a) exhibits the same characteristic peaks observed in pure spectra of Pani samples (curve b) and in the γ-$Fe_2O_3$ (curve c). This was taken as evidence of the presence of the two species (iron oxide and Pani) in the MNC, as follows: (i) the peak at 3420 $cm^{-1}$ correspond to the NAH stretching vibration of PANI [J. Magn. Magn. Mater. 314 (2007) 93-99.], (ii) the bands at 2919 $cm^{-1}$ and 2850 $cm^{-1}$ may be attributed to the symmetric and asymmetric stretching of the —$CH_2$— groups, respectively, (iii) the peaks at 1566 $cm^{-1}$ and 1482 $cm^{-1}$ are due to C=C stretching of the quinoid and benzenoid rings, respectively, while the peak at 800 $cm^{-1}$ is attributed to C—H out of plane deformation in the benzenoid ring [React. Funct. Polym. 68 (2008) 57-62], (iv) the peaks at 1295 $cm^{-1}$ and 1242 $cm^{-1}$ are related to C—N stretching vibration of the benzenoid ring [Nanotechnology 17 (2006) 5019.], and, finally, (v) the peaks at 636 $cm^{-1}$ and 585 $cm^{-1}$ are due to Fe—O vibrations.

EXAMPLE 5

DNA Retrieval Using the Magnetic Nanocomposite (MNC)

Figure 13:
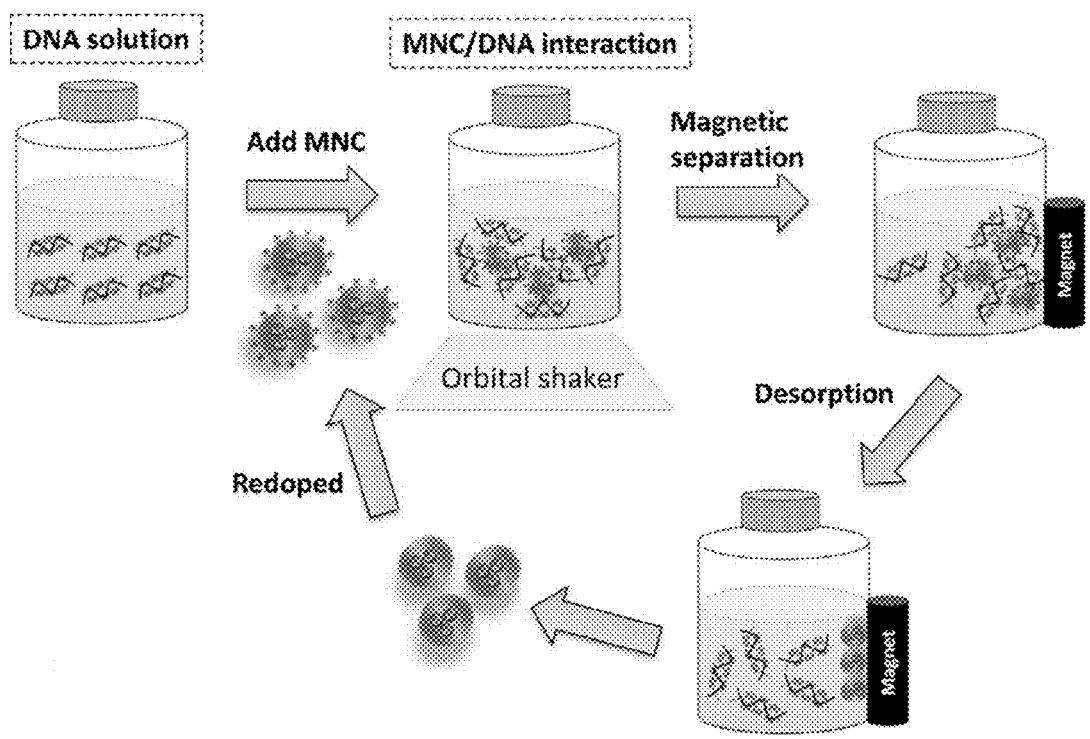
FIG. 13 is a schematic diagram of different steps involved in the procedure used to achieve DNA retrieval and desorption.

The present disclosure further relates to a method for retrieval of a nucleotide sequence such as RNA or DNA with the magnetic nanocomposite. The process includes, mixing iron chloride tetrahydrate with iron (III) chloride hexahydrate in solution; adding ammonium hydroxide ($NH_4OH$) to the mixture and stirring to form γ-$Fe_2O_3$ nanoparticles; stirring the γ-$Fe_2O_3$ nanoparticles in a solution with an inorganic acid, a surfactant and a monomer precursor of a conducting polymer; initiating polymerization of the monomer by adding the inorganic acid and an oxidizing agent to the stirred solution and further stirring to yield PANI/γ-$Fe_2O_3$ nanocomposites; adding the nanocomposites to an first aqueous solution of the nucleotide sequence and stirring so as to electrostatically interact the nanocomposites with the nucleotide sequence; and weakening the electrostatic interaction between the nanocomposite and the nucleotide sequence to recover the nanocomposite independently of the nucleotide sequence. For example, the FIG. 13 illustrates a schematic summarizing all the steps for DNA retrieval.

In an example, iron chloride tetrahydrate is mixed with iron chloride hexahydrate in a molar ratio of 1:2. Further, the process includes doping the nanocomposites with one or more acids. Moreover, stirring the γ-$Fe_2O_3$ nanoparticles in a solution with hydrochloric acid, sodium dodecyl sulfate and a monomer further includes stirring the γ-$Fe_2O_3$ nanoparticles in a solution with hydrochloric acid, sodium dodecyl sulfate and aniline. Also, adding the inorganic acid and an oxidizing agent to the stirred solution further includes adding ammonium persulfate to the stirred solution. Further, stirring the γ-$Fe_2O_3$ nanoparticles in a solution with an inorganic acid, a surfactant and a monomer precursor of a conducting polymer further includes stirring in a solution with sodium dodecyl sulfate. Moreover, stirring the γ-$Fe^2O_3$ nanoparticles in a solution with an inorganic acid comprises stirring with hydrochloric acid.

Additionally, after recovering the nanocomposite independently of the nucleotide sequence, the nanocomposite is washed and acid doped then added to a second aqueous solution of nucleotide sequence and stirred so as to electrostatically interact the nanocomposite with the nucleotide sequence of the second solution. Moreover, electrostatically interacting the nanocomposites with the nucleotide sequence further comprises electrostatically interacting with DNA or RNA. Furthermore, weakening the electrostatic interaction between the nanocomposite and the nucleotide sequence to recover the nanocomposite independently of the nucleotide sequence comprises weakening with a solution of an alkali salt. Further, weakening with a solution of an alkali salt comprises weakening with a solution of sodium hydroxide. The steps as mentioned herein, for DNA retrieval, are further explained in greater detail in conjunction with specific Examples.

In an example method for DNA retrieval using the magnetic nanocomposite synthesised in Example 4, 10 mL of a 50 mg/L sperm salmon DNA solution in a glass flask may be agitated using an orbital shaker operating at 230 rpm to achieve a good interaction between the MNC and DNA. After magnetic decanting of the MNC with a rectangular handheld 1 T magnet as illustrated in FIG. 13, the DNA concentrations may be determined by measuring absorbance at 260 nm. Different doses of MNC (1 mg, 2 mg, 3 mg and 4 mg) in 10 mL of a 50 mg/L SS-DNA, emphasize the capacity of the Pani/γ-Fe$_2$O$_3$ MNC for DNA retrieval as a function of the interaction time (5, 10, 30, 60, 120, 180 and 240 min). Also, the adsorption capacity of the MNC as a function of the concentration (5, 7.5, 10, 12.5, 15, 20, 25, 30, 40 and 50 mg/L) of SS-DNA in the solution may be evaluated.

The degree of DNA adsorption on the MNC is estimated as $$\% \text{ Adsoprtion} = \frac{C_0 - C_e}{C_0} \times 100$$

Where, $C_0$ and $C_e$ are the initial and final DNA concentration (mg/L) in the solution, respectively.

As a surface-based process, adsorption is a consequence of minimization of the surface energy of the particles. The exact nature of the DNA/MNP bonding depends on the details of the species involved. For a better understanding of the process, adsorption isotherms may be constructed to fit experimental data to the Langmuir and Freundlich models [Synth. Met. 160 (2010) 762-767; and, J. Ind. Eng. Chem. 18 (2012) 948-956.].

The adsorption capacity of the MNC may be calculated as $$q_e = \frac{V(C_0 - C_e)}{m}$$

where $q_e$ is the amount of DNA adsorbed per MNC mass unit (mg/g), V is the volume of the solution, $C_0$ is the initial (mg/L) concentration of the DNA solution, $C_e$ is the equilibrium concentration of DNA solution (mg/L), and m is the mass (in g) of the MNC used.

EXAMPLE 5.1

Effect of Interaction Time and MNC Dose

The MNCs prepared in accordance with the present methods exhibit a high DNA adsorption capacity. Introducing different amounts (1, 2, 3, and 4 mg) of Pani/γ-Fe$_2$O$_3$ MNC in a flask containing 10 mL of 50 mg/L solution of single stranded (SS)-DNA and thereafter adjusting the pH to 3.8 results in different rates of electrostatic interaction between the Pani chains and the double-stranded SS-DNA. At varying exposure times, the DNA-loaded MNC was magnetically decanted and the 260 nm absorbance of the now DNA-depleted solution was measured at varying exposure times to establish fractional adsorption as a function of interaction time.

Figure 14:
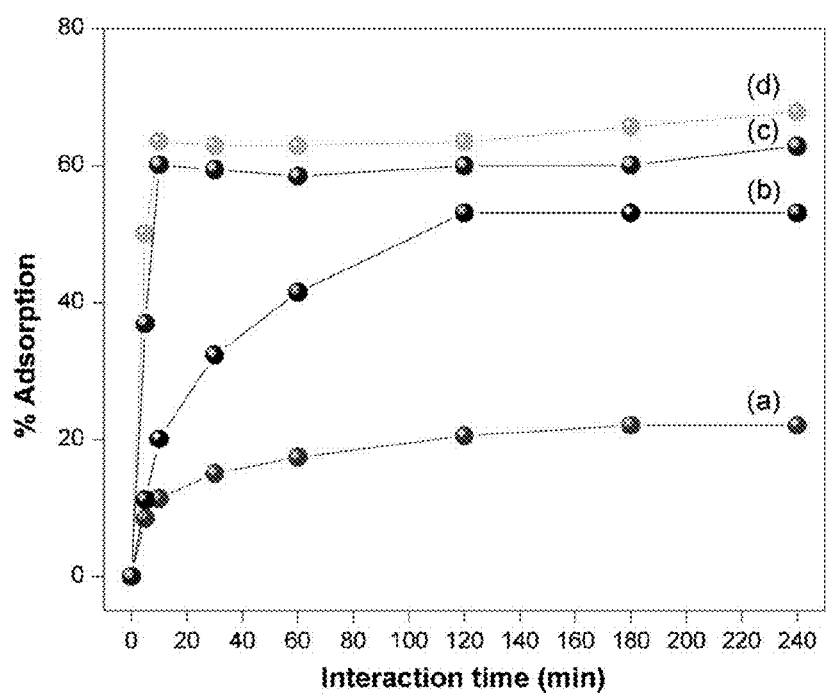
FIG. 14 is effect of interaction time on the DNA retrieval by the Pani/$\gamma$-$Fe_2O_3$ MNC.

A plot of the relations for the four different amounts of Pani/γ-Fe$_2$O$_3$ is represented by FIG. 14. It may be observed that with increasing interaction time, the DNA adsorption increases until reaching a maximum when the MNC becomes completely saturated with DNA, i.e. the system reaches an equilibrium where the MNC is not able to adsorb additional DNA from the solution. When 1 mg of the Pani/γ-Fe$_2$O$_3$ MNC is added (curve a), the removal process takes longer, since a time of 180 min is required for the MNC to reach its maximum adsorption (22%). On the other hand, by adding only 2 mg of MNC (curve b) to the SS-DNA solution, the removal process may be gradually increased so that the maximum adsorption capacity (53%) is observed at 120 min of interaction time. A much faster response may occur when higher doses of the MNC are used: for the 3 mg (curve c) and 4 mg (curve d) cases, the adsorption increases quickly and, in both instances, a waiting time of only 10 min is required to reach the observed saturation values of the MNC at 60% and 64% of the nominal limit, respectively.

EXAMPLE 5.2

Effect of DNA Concentration

Figure 15:
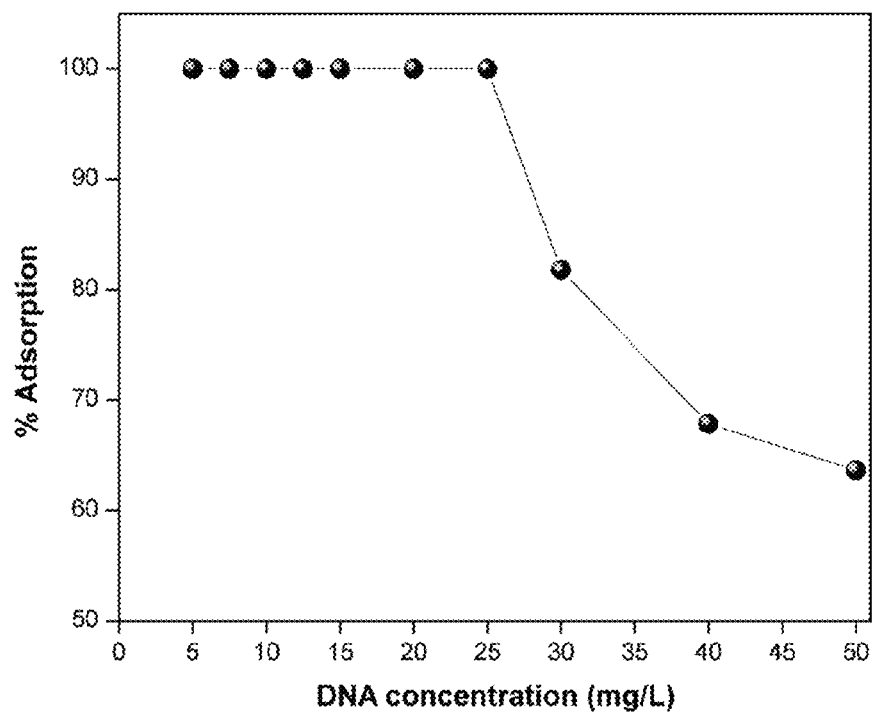
FIG. 15 is effect of the DNA concentration on the retrieval capacity of the Pani/$\gamma$-$Fe_2O_3$ MNC.

Adsorption of DNA onto the nanocomposite is related to the concentration of DNA solution. In view of the adsorption performance of the 4 mg sample of Example 5.1 as represented in FIG. 15, 4 mg of Pani/γ-Fe$_2$O$_3$ MNC may be used to determine the effect of DNA concentration upon % adsorption, To examine how to approach the nominal 100% limit of retrieval, a fixed amount of 4 mg of the MNC may be added to various RNA solutions or various solutions of SS-DNA having varying concentrations in the 5-50 mg/L range and the corresponding degree of DNA captured. As represented in FIG. 15, the data indicate that full retrieval was achieved for cases in which DNA solution concentrations are equal to or less than 25 mg/L. For solutions with concentrations equal to 30 mg/L, 40 mg/L and 50 mg/L, nominal capabilities of 82%, 68%, 64% may be observed, indicating that the saturation limit of the MNC may have been reached before removal of all DNA chains present in the solution was possible.

EXAMPLE 5.3

Desorption Experiments

By changing the pH of the solution it is possible to achieve an almost complete release of the DNA captured by the MNC. For example, 4 mg of Pani/γ-Fe$_2$O$_3$ MNC are added to a flask containing 10 mL of a 50 mg/L SS-DNA solution (pH 6). After 10 min of interaction, the pH of the solution drops to 3.8, and the MNC has captured 64% of its nominal capacity.

Figure 16:
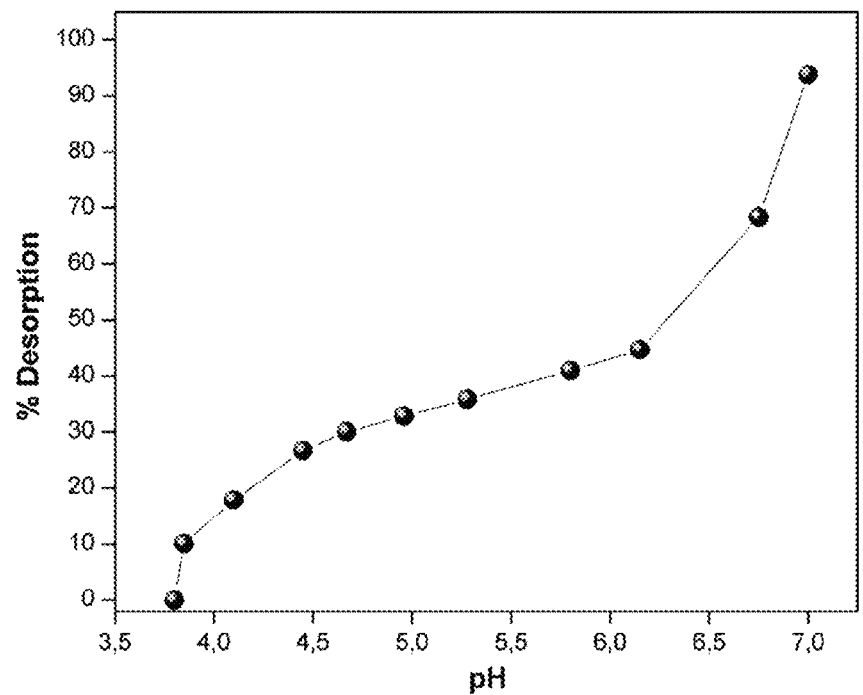
FIG. 16 is DNA desorption process of the Pani/$\gamma$-$Fe_2O_3$ MNC as a function of the pH.

Subsequent increase in the pH by addition of small volumes of NaOH may be effected. Measurement of absorbance at 260 nm yields an estimate of the fractional capability of the MNC after a series of additions of NaOH. The plot of FIG. 16 illustrates percentage of DNA desorbed as a function of the pH of the system. For pH values between 3.8 and 6.2 the desorption process is slow: only 45% of the captured DNA were released at a pH=6.2. However, the rate of desorption may be observed to increase dramatically thereafter, and 96% of the DNA is again dissolved in the solution when the pH reaches the value of 7.0. In an acidic environment, the protonated Pani chains have several positively charged active sites that can interact with the laterally positioned negative phosphate groups in the DNA double-chains. After the addition of NaOH, however, these sites become deprotonated, leading to a drastic reduction in the number of active sites in the MNC still able to continue to interact with the DNA molecules. As a whole, the desorption process proved to be simple and fast, taking about 2 min for all DNA to become desorbed from the Pani/γ-Fe$_2$O$_3$ MNC.

EXAMPLE 5.4

Adsorption Isotherm

Isotherm adsorption describes the amount of DNA adsorbed at the MNC surface as a function of the DNA present in the solution. Collected data for the SS-DNA adsorption isotherms on Pani/γ-Fe$_2$O$_3$ MNC may be fitted to both the Langmuir and Freundlich isotherm models.

The Langmuir isotherm model, valid for a monolayer adsorption of a species onto a surface containing a finite number of identical adsorption sites, may be expressed in a linear form as:

$$\frac{C_e}{q_e} = \frac{1}{bq_m} + \frac{C_e}{q_m}$$

where $q_e$ is the amount (in mg) of DNA adsorbed per mass unit (g) of MNC, $C_e$ is the final concentration of DNA (mg/L) in the solution after that the MNC was completely saturated (i.e. its maximum adsorption capacity was reached), and b and $q_m$ are constants. Physically, b (given in L/mg) is related to the energy of adsorption, while $q_m$ (given in mg/g) is the maximum adsorption capacity of DNA. Then, a plot of $C_e/q_e$ vs. $C_e$ would give a straight line that intercepts the $C_e/q_e$-axis in $1/(bq_m)$ and has a slope of $1/q_m$.

On the other hand, the Freundlich isotherm model, which assumes that the adsorbent consists of a heterogeneous surface composed of different classes of adsorption sites can be expressed in its linearized logarithmic form as:

$$\log q_e = \log K_F + \frac{1}{n}\log C_e$$

where $K_F$ and n are constants related to the adsorption capacity and adsorption intensity, to be graphically obtained from the linear plot log $q_e$ vs. log $C_e$.

Figure 18:
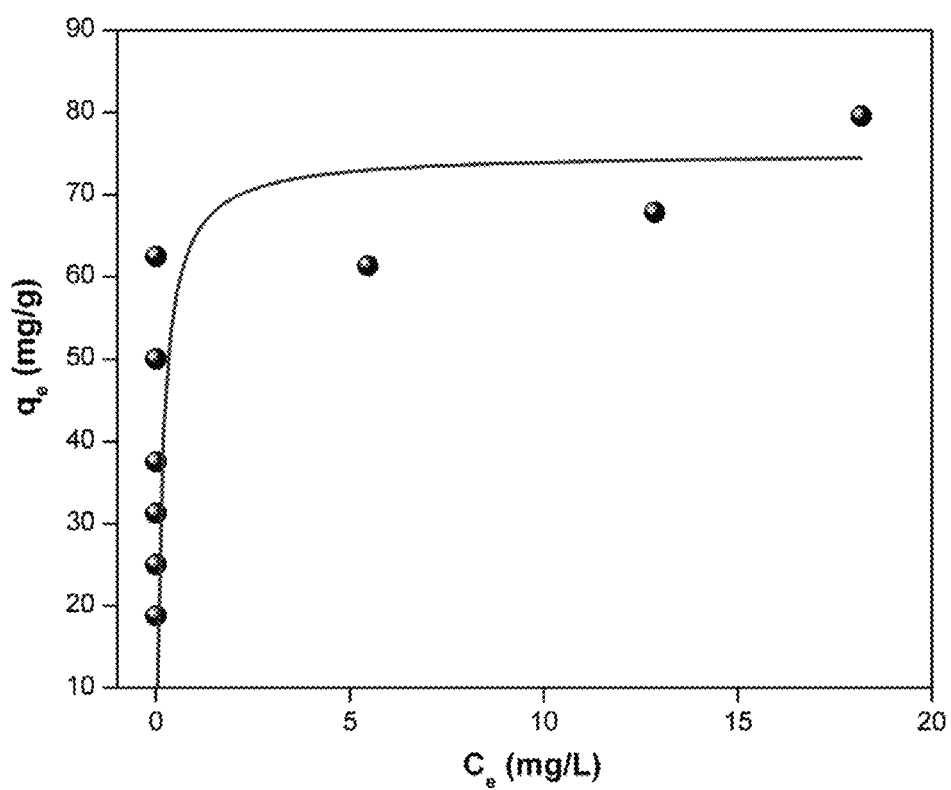
FIG. 18 is DNA adsorption isotherm onto Pani/$\gamma$-$Fe_2O_3$ MNC of the experimental values (special dot) and Langmuir model (line).

The values of the Langmuir and Freundlich adsorption isotherms parameters are presented in Table 1 of FIG. 17, together with the corresponding correlation coefficient R$^2$. In FIG. 18, the best fit of collected data for DNA adsorption by the MNC to the Langmuir model is depicted. The data indicate that the adsorption of SS-DNA adsorption onto the Pani/γ-Fe$_2$O$_3$ MNC may be better described by the Langmuir isotherm model, which estimates the maximum adsorption capacity $q_m$ as 75.2 mg DNA/g MNC.

EXAMPLE 5.5

Reusability of the MNC

The cost-effectiveness of MNC as presently disclosed is additionally improved by its ability to be desorbed and reused successfully after at least three regeneration steps without important losses in its adsorption capacity. This is described in detail in the following examples.

Pani/γ-Fe$_2$O$_3$ MNC is reusable in a series of nucleotide sequence retrievals. In an method designed to assess how many times the Pani/γ-Fe$_2$O$_3$ MNC can be effectively recycled, an amount of the disclosed MNC used in a previous desorption process and without DNA may be collected, washed with deionized water and HCl, and then added to 10 mL of a fresh 50 mg/L solution of SS-DNA. When this process is repeated three times and the $q_m$ for each cycle of adsorption-desorption determined, where $q_m$ was the maximum adsorption capacity, the value of $q_m$ observed in the second cycle is 96.5% of the total value obtained in the first cycle and in the third cycle is 90%. It follows that the Pani/γ-Fe$_2$O$_3$ MNC may be reused successfully after at least three regeneration steps, without significant loss in its adsorption capacity. One having ordinary skill in the art can appreciate that enriching the DNA content in an originally very dilute DNA solution may be achieved, by following several cycles of capture, magnetic separation and subsequent release of DNA in a smaller recipient solution.

EXAMPLE 5.6

Interaction Mechanism

As the usefulness of the described MNC depends on effective adsorption and desorption of nucleic acids, the mechanism of interaction between the nucleic acids and the MNCs is of interest. In one aspect, interaction between the MNC and the DNA chains results from their mutual electrostatic interaction. To investigate the MNC/DNA zeta potential (ζ) measurements were performed for the MNC dispersed in water, the pure DNA solution and the DNA solution after the interaction with the MNC. In the case of MNC dissolved in water, a ζ value of 4.2 mV (pH 3.8) was obtained, while the much more stable DNA solution had a ζ value of 54 mV (pH 6). Finally, the ζ value of the DNA solution decreased to 3 mV (pH 3.8) after the interaction had taken place and the magnetic decantation of the MNC had been implemented. This reduction in the ζ value implies that when the DNA chains were captured, there was a decrease in the total number of negative charges per dissolved particle. This is entirely consistent with the idea that the interaction mechanism corresponds to the electrostatic attraction between the positive charges present in the Pani chains of the MNC and the negatively charged phosphate groups of the DNA molecules.

EXAMPLE 6

A Biological Diagnosis Kit for Rapid Patient Diagnosis

The present disclosure also relates to a biological diagnosis kit for rapid patient diagnosis employing the DNA-bonding nanocomposite for DNA retrieval within the kit. In an embodiment, the kit includes at least one composite, at least one short nucleotide sequence, and an appropriate substrate for the immobilization of the short nucleotide sequence such as RNA or a single-stranded DNA as well as a genetic sample of the patient. In an example, the composite includes at least one magnetic nanoparticle such as maghemite and at least one conducting polymer such as PANI. In another example, the at least one composite include a fluorescent composite. In yet another example a substrate in the form of a glass slide, paper and/or a polymer strip may also be provided.

In an embodiment, the oxidizing agents iron chloride tetrahydrate and iron (III) chloride hexahydrate contribute oxidation to the DNA-bonding nanocomposite.

On exposure to the patient genetic material, the DNA bonding nanocomposite bonds with the DNA. The DNA content in an originally very dilute DNA solution (patient genetic material or any biological sample for analysis) can be enriched, by following several cycles of capture, magnetic separation and posterior release of DNA in a smaller recipient. It is to be understood that, the procedure of molecular diagnosis may be sharpened with a thus enriched DNA solution. A fluorescent composite may facilitate the biological analysis.

The presently disclosed MNC has an estimated adsorption capacity significantly higher than many other adsorbents. Table 2 of FIG. 19 presents data related to adsorption characteristics of the presently disclosed MNC relative to other known adsorbents. While magnetic mesoporous silica has been reported as having a $q_m$ value as high as 121.6 mg/g, this maximum amount of DNA adsorption did not occur until 1200 min. In contrast, the MNC of the present disclosure required just 10 minutes to reach maximum DNA adsorption. It should be noted that a smaller particle size resulting in a larger surface area available for adsorption may offer significant contribution to reaching a high maximum adsorption capacity in a short amount of time. Thus, in an embodiment, the disclosed MNC may include individual particles with sizes within the nano-scale range. For example, the MNC may have an average diameter value of approximately 14 nm.

The skilled in the art will immediately recognize the value of the present teachings and they also will understand that variations in the forms of executing the disclosure herein exemplified must be considered as within the spirit of the present disclosure and in the general scope of the accompanying claims.

The invention claimed is:

1. A process for retrieval of a nucleotide sequence, comprising:
   in solution, mixing an iron chloride tetrahydrate with an iron (III) chloride hexahydrate, to form a mixture;
   adding an ammonium hydroxide to the mixture and stirring to form maghemite nanoparticles;
   stirring the maghemite nanoparticles in the solution with an inorganic acid, a surfactant and a monomer precursor of a conducting polymer;
   initiating polymerization of the monomer precursor by adding the inorganic acid and an oxidizing agent to the stirred solution and further stirring to yield polyaniline/maghemite nanocomposites;
   adding the nanocomposites to a first aqueous solution of the nucleotide sequence and stirring so as to electrostatically interact the nanocomposites with the nucleotide sequence; and
   weakening the electrostatic interaction between the nanocomposites and the nucleotide sequence to recover the nanocomposites independently of the nucleotide sequence.

2. The process as set forth in claim 1, wherein mixing the iron chloride tetrahydrate with the iron (III) chloride hexahydrate further comprising mixing in a molar ratio of 1:2.

3. The process as set forth in claim 1, further comprising doping the nanocomposites with one or more acids.

4. The process as set forth in claim 1, wherein after recovering the nanocomposites independently of the nucleotide sequence, the nanocomposites are washed and acid doped then added to a second aqueous solution of nucleotide sequence and stirred so as to electrostatically interact the nanocomposites with the nucleotide sequence of a second solution.

5. The process as set forth in claim 1, wherein stirring the maghemite nanoparticles in the solution with the inorganic acid, the surfactant and the monomer further comprises stirring the maghemite nanoparticles in a solution with aniline.

6. The process as set forth in claim 1, wherein stirring the maghemite nanoparticles in the solution with the inorganic acid, the surfactant and the monomer precursor of the conducting polymer further comprises stirring the maghemite nanoparticles in the solution with the inorganic acid, a sodium dodecyl sulfate and the monomer precursor.

7. The process as set forth in claim 1, wherein stirring the maghemite nanoparticles in the solution with the inorganic acid further comprises stirring in the solution with a hydrochloric acid.

8. The process as set forth in claim 1, wherein adding the inorganic acid and the oxidizing agent to the stirred solution further comprises adding an ammonium persulfate to the stirred solution.

9. The process as set forth in claim 1, wherein electrostatically interacting the nanocomposites with the nucleotide sequence further comprises electrostatically interacting with a DNA or an RNA.

10. The process as set forth in claim 1, wherein the weakening of the electrostatic interaction between the nanocomposites and the nucleotide sequence to recover the nanocomposites independently of the nucleotide sequence further comprises weakening with a solution of an alkali salt.

11. The process as set forth in claim 10, wherein the weakening with the solution of the alkali salt further comprises weakening with a solution of sodium hydroxide.

* * * * *